United States Patent [19]
Ellison

[11] 3,990,960
[45] Nov. 9, 1976

[54] OIL TEST APPARATUS
[75] Inventor: Lynn E. Ellison, Crystal Lake, Ill.
[73] Assignee: Naeco Associates, Inc., Arlington, Va.
[22] Filed: Nov. 26, 1975
[21] Appl. No.: 635,455

Related U.S. Application Data

[63] Continuation of Ser. No. 471,749, May 20, 1974, abandoned, which is a continuation of Ser. No. 304,864, Nov. 8, 1972, abandoned, which is a continuation of Ser. No. 106,884, Jan. 15, 1971, abandoned, which is a continuation of Ser. No. 724,977, April 29, 1968, abandoned.

[52] U.S. Cl. ............................................. 204/195 R
[51] Int. Cl.² ................. G01N 27/46; G01N 27/50; G01N 27/52
[58] Field of Search .......... 204/1 T, 195 R; 324/29, 324/30 R, 30 B

[56] References Cited
UNITED STATES PATENTS

| | | | |
|---|---|---|---|
| 1,865,847 | 7/1932 | Ennis | 204/195 R X |
| 2,122,578 | 7/1938 | McMaster et al. | 324/30 UX |
| 2,215,213 | 9/1940 | Ellis | 204/195 R X |
| 2,782,151 | 2/1957 | Suthard | 204/1 T |
| 3,258,682 | 6/1966 | Maurer | 324/30 |

*Primary Examiner*—G. L. Kaplan
*Attorney, Agent, or Firm*—Olson, Trexler, Wolters, Bushnell & Fosse, Ltd.

[57] ABSTRACT

A method and apparatus for testing the lubricating quality of oil. The apparatus comprises a pair of dissimilar, spaced-apart electrodes, a voltage indicator and circuitry interconnecting the electrodes and the voltage indicator. Upon placing an oil sample between and in contact with the electrodes, oxidation by-products in the oil, built up therein due to deterioration or breakdown of the oil, react with one of the electrodes to form an oxide thereof. The oxidation of the electrode produces a corresponding voltage reading which indicates the lubricating quality of the oil.

13 Claims, 5 Drawing Figures

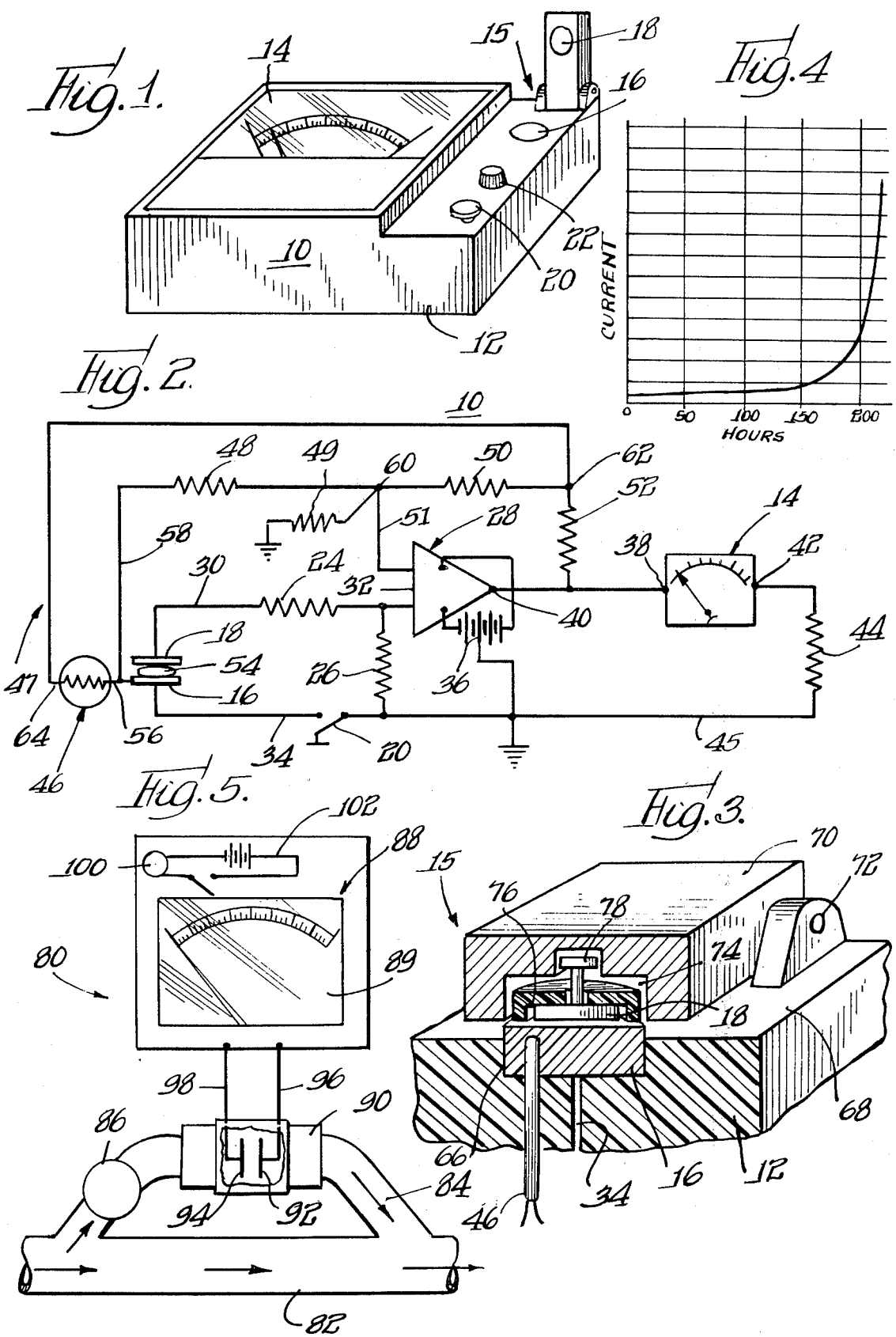

OIL TEST APPARATUS

This is a continuation of application Ser. No. 471,749, filed May 20, 1974 which in turn was a continuation of application Ser. No. 304,864, filed Nov. 8, 1972 which in turn was a continuation of application Ser. No. 106,884, filed Jan. 15, 1971 which in turn was a continuation of application Ser. No. 724,977, filed Apr. 29, 1968, each now abandoned.

BACKGROUND OF THE INVENTION

This invention relates generally to oil testing methods and apparatus, and more particularly to a method and apparatus for testing the lubricating condition of engine oils.

Synthetic lubricating oils used in internal combustion engines, such as, for example, aircraft engines, contain engine additives which are blended in the oil to enable it to withstand higher temperatures, etc., before oxidation and acid build-up occurs. Also added to the oil is what is known as an inhibitor. Its purpose is to consume oxidation by-products as they are formed in the oil in an attempt to prolong the life of the oil.

Even with the above described additives and inhibitors, oil eventually breaks down and is no longer a satisfactory lubricant. The inhibitors eventually lose their ability to consume any additional oxidation by-products and become depleted. When this occurs, an engine in which the oil is used may be damaged, partially or completely so as to require a complete overhaul. This can be costly both monetarily and, in the case of aircraft engine breakdown, in human life.

Several oil testing techniques are now in use to periodically determine the lubricating state or condition of oil being used in aircraft or the like engines. These tests are: The titration test which measures the acid content of oil samples (acid build-up thought of as being indicative of an unsatisfactory oil); spectroanalysis, wherein the percentages of oxides and acids formed in the oil are determined; and electrical conductivity wherein the ability of the oil to be electrically conductive is determined (the resistivity of the oil indicating the degradation thereof).

All of the methods require that a sample of the oil taken from the engine be transported to a laboratory to be tested by equipment located thereat. This procedure normally takes about 3 full days before a report can be obtained. In most instances, especially in the case of aircraft, an airline cannot wait the full 3 days and schedules the aircraft back into service without receiving the test data. This often results in damaged aircraft engines, or even a disastrous plane crash.

SUMMARY OF THE INVENTION

Accordingly, it is a general object of this invention to provide a new and improved method and apparatus for determining the lubricating qualities of engine oil which overcomes the shortcomings and disadvantages of the prior art methods and apparatus.

It is another object of this invention to provide a method and apparatus of the above-described type which provides accurate results in a minimum of time.

It is a more specific object of this invention to provide oil testing apparatus which rapidly and accurately indicates the build-up of oxidation by-products formed in an engine oil sample and thereby discloses the lubricating condition of the oil from which the sample is taken.

It is yet another specific object of this invention to provide oil testing apparatus which indicates the depletion of inhibitors provided in the oil for consumption of the oxidized by-products formed therein.

It is a further object of the present invention to provide oil testing apparatus of the above-described type which is portable and can easily be used at the site of the engine wherein the oil to be tested is located.

It is yet another object of the present invention to provide oil testing apparatus of the above-described type which may be mounted in the oil line of an internal combustion engine to provide a constant indication of the condition of the oil therein.

It is still another object of this invention to provide a method for testing the lubricating qualities of engine oil which is simple, easy to perform and provides an accurate indication of the condition of the oil.

DESCRIPTION OF THE DRAWINGS

A better understanding of the present invention and its organization and construction may be had by referring to the description below in conjunction with the accompanying drawings, wherein:

FIG. 1 is a perspective view of lubricating oil testing apparatus according to the invention;

FIG. 2 is a schematic diagram of the circuitry of the oil testing apparatus of FIG. 1;

FIG. 3 is an enlarged sectional perspective view of the testing electrodes of the oil testing apparatus of FIG. 1;

FIG. 4 is a chart illustrating the breakdown of lubricating oils over a period of engine hours; and FIG. 5 is a schematic representation of an in-line oil testing apparatus according to the invention.

DETAILED DESCRIPTION

Referring now to the drawings more in detail, FIG. 1 thereof illustrates an oil testing device 10 according to the invention. The device or apparatus, as shown, includes a housing 12 having mounted thereon a high impedance voltmeter 14 and an electrode assembly 15 including a pair of dissimilar electrodes 16 and 18. Electrode 16 is constructed of a metal or composition of metals from the electromotive force series, including cadmium, aluminum, silver, gold, etc. Electrode 18 is preferably a noble metal, such as platinum, etc. An operating button 20 and a scale selector knob 22 are provided also on the housing 12. Electrode 18 may also be of the stainless steel series.

Looking at FIG. 2, there is shown a schematic diagram of the circuitry of the oil testing device 10 of FIG. 1. Electrodes 16 and 18 are shown connected through a voltage dividing network comprising resistors 24 and 26, to the input 32 of an amplifier 28; electrode 18 being connected via a lead 30 to a resistor 24 which in turn is connected to the input 32 of amplifier 28 and the other electrode 16 being connected via lead 34 and switch 20 to ground, and resistor 26 being connected between ground and the input 32 of the amplifier. A battery 36 is connected to amplifier 28 to power the latter, and one side 38 of the voltmeter 14 is connected to the output 40 of the amplifier 28, while the other side 42 of the voltmeter 14 is connected through a resistor 44 to ground via lead 45. A temperature compensating network 47, including a thermistor 46 and resistors 48, 50 and 52, is provided to compensate for temperature differences in the oil samples being tested. As can be seen in FIG. 2, thermistor 46 is connected to the electrode 16 whereon an oil sample 54 is placed for testing. One side 56 of the thermistor 46 is connected in series via lead 58 to resistor 48. Resistor 48, grounded resistor 49, an input lead 51 to amplifier 28 and resistor 50 are connected at junction 60. Resistor 50 is in turn connected at junction 62 both to the other side 64 of thermistor 46 and through resistor 52 to the output 40 of amplifier 28.

Referring now to FIG. 3, there is shown therein an enlarged sectional view of the electrode assembly 15. The lower electrode 16 of the assembly is mounted directly in a cavity or recess 66 provided in the upper surface 68 of housing 12. The electrode 16 is connected by means of a lead 34 (FIG. 2) to a ground connection within the housing 12. Thermistor 46 is embedded in housing 12 and extends into electrode 16 as shown in FIG. 3. The upper electrode 18 is mounted within a block or housing portion 70 which is pivotally mounted by means of a pair of hinged mounting members 72 to the upper surface 68 of housing 12. The hinged block is so mounted that, upon pivoting the block downwardly toward surface 68, the dissimilar electrodes 16 and 18 will be in direct parallel alignment, the exposed faces of the electrodes being flat.

As can be seen in FIG. 3, electrode 18 is mounted in a cavity 74 in the block 70 and is insulated from the block. An insulating member 76 provided about the electrode 18 extends outwardly from the cavity 74 a distance slightly greater than the electrode 18 itself, so that, upon moving the block 70 into a mating position with electrode 16, the insulating member 76 will rest on electrode 16 and hold electrode 18 spaced from the latter. A preferable distance between the electrodes is 0.002 of an inch. A T-shaped electrode extension 78 extends inwardly into the block 70 from electrode 18 and is connected via lead 30 (not shown in FIG. 3) to resistor 24, etc., as illustrated in FIG. 2. The housing 12 surrounding electrode 16 is made of a material, such as, for example, aluminum, and serves to shield the electrode assembly from outside electrical interference.

It is advantageous now to provide a detailed description of the operation of the oil testing device 10 heretofore described.

The functioning of the test apparatus is based on the discovery that as lubricating oil deteriorates (i.e., when the inhibitors, additives, etc., added thereto can no longer consume oxidized by-products in the oil) the rate of oxidation by-product build-up within the oil increases. When the oxidation by-products formed in the oil become too plentiful, the oil cannot withstand high stress or temperature, and can no longer satisfactorily lubricate an engine. Thus, metal-to-metal wear within the engine takes place, and eventually causes the breakdown thereof. In an aircraft, this may mean an engine failure on take off.

The oil testing apparatus according to the invention is provided to aid in the prevention of engine breakdown due to deteriorated oil. When an oil sample taken from an engine is placed between the electrodes 16 and 18 of the testing device 10, oxides present therein will cause an oxidation reaction to take place with the electrode 16, comprised of a metal or metals from the electromotive force series, to form an oxide thereof. The oxidation of the electrode 16 produces a corresponding voltage output across resistor 26. This voltage output is amplified by the amplifier 28 (FIG. 2) to effect a voltage reading on the meter 14. The greater the amounts of oxidation by-products present in the oil sample, the less the resistance to the flow of current between electrodes 16 and 18 and the greater the current produced. Consequently, a higher voltage reading appears on the meter 14.

In the use of the embodiment of the invention of the type shown in FIG. 1, the electrodes 16 and 18 are first cleaned of all foreign matter, such as, on electrode 16, oxides formed from the oxidation of the electrode due to oxygen in the air, etc. This may be performed with a suitable oxide removing solution. After the electrodes are thoroughly cleaned, a sample of oil taken from an engine is placed on the lower electrode 16. The hinged block 70 is pivoted about until insulating member 76 contacts electrode 16 and the electrodes 16 and 18 are in a spaced, parallel relation, as shown in FIG. 3. The oxidation by-products present in the oil sample react with the electrode 16 to produce an oxide thereof (i.e., for example, in the case of aluminum, aluminum oxide). Button 20 is depressed to complete the circuit of the device (FIG. 2) and a voltage reading, caused by the current produced by the oxidation of the electrode, is given on voltmeter 14, indicating the amount of oxidation by-product build-up in the oil sample and hence the lubricating quality of the oil. The temperature of oil samples may vary but, due to the provision of the temperature compensating network 47, these temperature differences are accommodated. Thus, the voltage readings on voltmeter 14 are relatively accurate regardless of the oil temperature.

The chart of FIG. 4, compiled through the use of a testing device according to the invention, indicates the operating hours of an engine using a particular oil, and current produced at intervals during these operating hours. It will be noted that at approximately 200 hours of engine running time, with this particular engine oil sample, the curve increases considerably and continues to climb at a steep rate. This serves to show that the time at which the oil should have been changed in the engine is indicated at the point of rapid increase of the curve.

As explained above, in the case of the testing device of FIG. 1, an oil sample must be taken from the engine and placed between electrodes 16 and 18. In FIG. 5, however, the testing device embodiment 80 has been designed to provide a constant indication of the lubricating quality of an oil, and also an indication as to when the oil should be changed in the engine.

Tube 82, representing an oil line of an internal combustion engine, has been provided with a by-pass section 84. The oil flow through by-pass section 84 is controlled by a valve 86 near the inlet thereof (the oil flow being in accordance with the direction of the arrows). Near the center of section 84 there is provided an electrode housing 90 containing a pair of electrodes 92 and 94 similar to 16 and 18 of FIG. 1. The electrodes are spaced from each other so that a quantity of oil flowing through section 84 is located therebetween.

A voltmeter 89, amplifier and circuitry like that of FIG. 2, are located in housing 88, and leads 96 and 98 serve to connect the circuitry with electrodes 92 and 94, respectively.

The operation of the in-line oil testing apparatus is similar to the one of FIG. 1, except that a sample of oil is always present between electrodes 92 and 94. As oxidation by-product build-up occurs in the oil, more voltage is indicated and, as a consequence, the electrode formed of a metal of the electromotive force series is oxidized. The oxidation of the electrode produces a corresponding voltage reading on the voltmeter 89. When the voltage reading produced by the oxidation of the electrode reaches a predetermined level, which may be determined through tests showing the deterioration of a particular engine oil, the light 100 is lit and, by means of auxiliary circuitry 102 of a well-known type, is kept lit to indicate that an oil change is in order.

Thus, either through the taking of an oil sample and immediately checking the condition thereof by means of the embodiment of FIG. 1, or by constantly checking the condition of an engine oil as it is being circulated, by means of the embodiment of FIG. 5, an accurate and reliable indication is given as to the lubricating quality of an engine oil.

While particular embodiments of the invention have been shown and described, it should be understood that the invention is not limited thereto, since many modifications may be made. It is therefore contemplated to cover by the present application any and all such modifications as fall within the true spirit and scope of the appended claims.

What is claimed is:

1. Apparatus for indicating the lubricating quality of engine lubricating oils adapted for high stress operating conditions as in aircraft and containing oxidation by-product inhibitors, by determining the amount of oxidation by-products in a sample of the engine lubricating oil after periods of use as the inhibitors lose effectiveness; and comprising housing means of portable nature for use at the site of testing and having a support surface, a pair of electrodes constructed of dissimilar metals having different rates of oxidation, means mounting said pair of electrodes on said support surface for relative movement therebetween for selective positioning thereof to facilitate placement of a discrete sample of the engine lubricating oil in contact with an electrode and to position the electrodes with adjacent surfaces thereof confronting each other in closely spaced relationship to provide a space therebetween for the discrete sample of the engine lubricating oil with the confronting electrodes positioned for contacting the oil sample therebetween and responsive to the presence of oxidation by-products by reaction of one of said electrodes to the amount of oxidation by-products in the oil sample for directly producing a flow of internally sourced current having a value proportional to said amount of oxidation by-products, and circuit means within said housing means electrically connected to said electrodes for electrically indicating the difference of oxidation rates of the two electrodes and thereby to reveal the lubricating quality of the oil sample being tested.

2. Apparatus as claimed in claim 1 wherein said one electrode comprises aluminum.

3. Apparatus as claimed in claim 1 wherein said one electrode comprises cadmium.

4. Apparatus as claimed in claim 1 wherein said one electrode is a composite of metals, one at least of which is in the electromotive force series.

5. Apparatus as claimed in claim 1 wherein the other electrode comprises a noble metal.

6. Apparatus as claimed in claim 1 wherein said circuit means includes a resistor having opposite ends electrically connected to respective electrodes and a voltmeter connected in parallel relation with said resistor, whereby said current flow induces a voltage across said resistor, the value of which is indicated on said voltmeter.

7. Apparatus as claimed in claim 6 wherein said circuit means includes means connected electrically intermediate said resistor and said voltmeter for amplifying said voltage.

8. Apparatus as claimed in claim 7 and further including a temperature compensating network electrically connected to said electrodes and to said amplifier means for varying said voltage in accordance with the temperature of said oil whereby to compensate for the temperature variations in samples of said oil.

9. Apparatus as claimed in claim 8 wherein said temperature compensating network includes a thermistor device connected to said one electrode.

10. Apparatus as claimed in claim 1, wherein one of said electrodes is fixedly mounted on said support surface and the other electrode is movably mounted on said support surface for movement away from confronting position relative to said one electrode to facilitate placement of an oil sample thereon.

11. Apparatus as claimed in claim 1, wherein a block member is pivoted on said support surface and carries said other electrode and spacer means maintaining said electrodes in closely spaced relationship when the electrodes are in confronting position for contacting the oil sample.

12. Apparatus as claimed in claim 11, wherein said block member is provided with a cavity opening toward said support surface with the spacer means disposed within the cavity.

13. Apparatus as claimed in claim 1, wherein the spacing between the electrodes when in confronting position is of the order of 0.002 of an inch.

* * * * *